United States Patent [19]

Hackenbruch et al.

[11] Patent Number: 5,250,738
[45] Date of Patent: Oct. 5, 1993

[54] PROCESS FOR THE PREPARATION OF 1,4-BIS(4-HYDROXYBENZOYL)-BENZENE

[75] Inventors: Joachim Hackenbruch, Ginsheim; Theodor Papenfuhs, Frankfurt am Main, both of Fed. Rep. of Germany

[73] Assignee: Hoechst Aktiengesellschaft, Frankfurt, Fed. Rep. of Germany

[21] Appl. No.: 778,162

[22] PCT Filed: Jun. 25, 1990

[86] PCT No.: PCT/EP90/01002
§ 371 Date: Feb. 24, 1992
§ 102(e) Date: Feb. 24, 1992

[87] PCT Pub. No.: WO90/00256
PCT Pub. Date: Jan. 10, 1991

[30] Foreign Application Priority Data

Jun. 30, 1989 [DE] Fed. Rep. of Germany ....... 3921449

[51] Int. Cl.$^5$ ............................................. C07C 45/64
[52] U.S. Cl. .................................... 568/316; 568/796
[58] Field of Search ................................. 568/796, 316

[56] References Cited

U.S. PATENT DOCUMENTS

| | | | |
|---|---|---|---|
| 4,022,795 | 5/1977 | Bamfield et al. | 568/316 |
| 4,504,689 | 3/1985 | Veracini | 568/796 |
| 4,691,058 | 9/1987 | Stegmann | 568/316 |

FOREIGN PATENT DOCUMENTS

| | | | |
|---|---|---|---|
| 94347 | 11/1983 | European Pat. Off. | 568/316 |
| 865595 | 12/1952 | Fed. Rep. of Germany | 568/316 |
| 59-219249 | 12/1984 | Japan | 568/316 |
| 405859 | 11/1973 | U.S.S.R. | 568/316 |
| 50405859 | 11/1973 | U.S.S.R. | 568/316 |

OTHER PUBLICATIONS

Chemical Abstracts vol. 80, 1974, (Columbus, Ohio, see p. 348 abstract 82351d.

Primary Examiner—James H. Reamer
Attorney, Agent, or Firm—Connolly and Hutz

[57] ABSTRACT

A process for the preparation of 1,4-bis(4-hydroxybenzoyl)benzene of the formula (I)

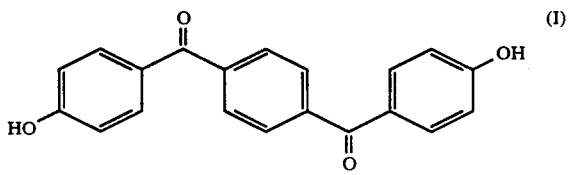

by reacting a 1,4-bis(4-halobenzoyl)benzene of the formula (II)

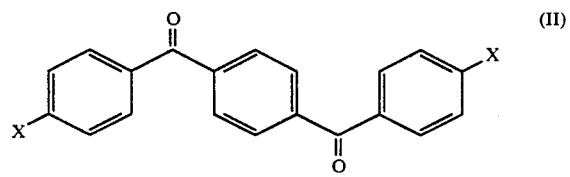

in which X is a fluorine, chlorine or bromine atom, with an alkali metal hydroxide or alkaline earth metal hydroxide or with mixtures of these hydroxides in a solvent which is inert to the reaction components under the reaction conditions at temperatures of about 100° C. to about 250° C., if appropriate in the presence of a phase transfer catalyst.

12 Claims, No Drawings

PROCESS FOR THE PREPARATION OF 1,4-BIS(4-HYDROXYBENZOYL)-BENZENE

DESCRIPTION

The present invention relates to an improved process for the preparation of 1,4-bis(4-hydroxybenzoyl)benzene by reaction of 1,4-bis(4-halobenzoyl)benzene with alkali metal hydroxides or alkaline earth metal hydroxides in various solvents at elevated temperatures.

1,4-Bis(4-hydroxybenzoyl)benzene is an important monomer compound for the preparation of industrial plastics and can be converted by reaction with 1,4-haloaromatics to give polyether ketones. Previous preparation methods are the Fries rearrangement of diphenyl terephthalate (J.A.C.S. 1938, 2284; EP 75,390), the dealkylation of 1,4-bis(4-methoxybenzoyl)benzene with HBr (Doroshenko, Vysokomol, Soedin 8(10), 1787–92, 1966) and the nucleophilic substitution reaction of 1,4-bis(4-chlorobenzoyl)-benzene with sodium hydroxide solution in water in the presence of copper salts (SU 405,859). It is common to these known preparation methods that they proceed with heavy environmental pollution using compounds which are hazardous to health and moreover expensive.

It has now been found that the nucleophilic replacement of the hydroxyl group by a halogen atom, in contrast to the process of SU-PS 405,859, is possible without copper in the presence of a solvent and that this solvent can be separated off by distillation after reaction is complete and recycled to the next reaction.

The invention thus relates to an improved process compared to the prior art for the preparation of 1,4-bis-(4-hydroxybenzoyl)benzene of the formula (I)

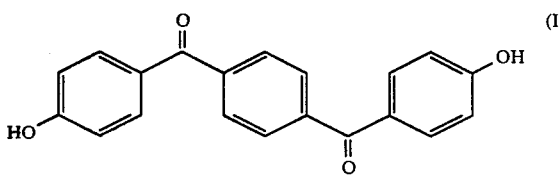

by reacting a 1,4-bis(4-halobenzoyl)benzene of the formula (II)

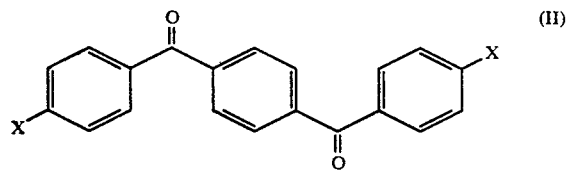

in which X is a fluorine, chlorine or bromine atom, with an alkali metal hydroxide, preferably lithium hydroxide, sodium hydroxide or potassium hydroxide, or with an alkaline earth metal hydroxide, preferably magnesium hydroxide or calcium hydroxide, or with mixtures of the abovementioned hydroxides, in a solvent which is inert to the reaction components under the reaction conditions or in a two-phase system of water and an inert organic solvent at temperatures from about 100° C. to about 250° C., preferably about 150° C. to about 220° C., if appropriate in the presence of a phase transfer catalyst.

As far as the amount of hydroxide used is concerned, advantageously about 200 to about 500 mol percent, preferably about 200 to about 250 mol percent, of hydroxide are employed per halogen atom to be replaced. The hydroxide can be added both as an aqueous solution and in anhydrous form, the use of aqueous hydroxide solutions being preferred because of their good meterability.

The phase transfer catalysts optionally employed are, for example, added in an amount from about 0.5 to about 30% by weight, relative to the hydroxide. Phase transfer catalysts of this type are described, for example, in Dehmlow/Dehmlow "Phase Transfer Catalysis", Verlag Chemie, Weinheim 1983 and are as a rule quaternary ammonium or phosphonium compounds, and also crown ethers or pyridinium compounds. Examples of these which may be mentioned are tetraalkylammonium chloride or bromide, tetraalkylphosphonium chloride or bromide, tetraphenylphosphonium chloride or bromide, distearyldimethylammonium choloride (sic) or bromide, hexadecyltributylphosphonium chloride or bromide, pyridinium chloride or bromide or 18-crown-6. In addition to an individual phase transfer catalyst, mixtures of various phase transfer catalysts can also be employed.

Examples of suitable inert solvents for the process according to the invention are chlorobenzene, dichlorobenzene, trichlorobenzene, xylene, toluene or chlorotoluene. In addition to organic inert solvents, two-phase systems composed of water and an organic inert solvent can also be used. Customarily, the reaction is carried out in a water/solvent mixture, the weight ratios of water:solvent being 50:1 to 1:20. After reaction is complete, the solvent is separated off by azeotropic distillation, if necessary with the addition of water. It can be recycled to the next reaction without loss.

The reaction can be carried out without pressure or under pressure. In the case of low-boiling solvents, the pressure procedure is advantageous.

The reaction times vary between about 2 and about 12 hours.

In German Patent 865,595, a process for the preparation of oxyaryl ketones is described in which halobenzophenones are reacted with alkalis, alcoholates or phenolates at relatively high temperatures. In the case of the reaction with caustic soda or caustic potash, the reaction is carried out in an aqueous medium.

The invention is explained in greater detail by the examples below, without being restricted thereto.

EXAMPLE 1

161.6 g (0.5 mol) of 1,4-bis(4-fluorobenzoyl)benzene, 83.7 g (2.05 mol) of NaOH, 2500 g of water and 200 g of chlorobenzene are placed in a stainless steel autoclave and heated at 200° C. for 7 hours with continuous stirring. After reaction is complete, 195 g of chlorobenzene are distilled off by azeotropic distillation. The orange solution is cooled to 50° C. and adjusted to pH=2 with 350 g of HCl (about 30% strength). The precipitated white 1,4-bis(4-hydroxybenzoyl)benzene is washed with water until neutral. After drying, 156 g (=98.0% of theory) having a solidification point of 318°–319° C. are obtained.

EXAMPLE 2

177.6 g (0.5 mol) of 1,4-bis(4-chlorobenzoyl)benzene, 83.7 g (2.05 mol) of NaOH, 2500 g of water and 200 g of chlorobenzene are placed in a stainless steel autoclave and heated at 220° C. for 7 hours with continuous stirring. After reaction is complete, 190 g of chlorobenzene are distilled off by azeotropic distillation. The orange solution is cooled to 50° C. and adjusted to pH=2 with 350 g of HCl (about 30% strength). The precipitated white 1,4-bis(4-hydroxybenzoyl)benzene is washed with water until neutral. After drying, 154 g (=96.8% of theory) having a solidification point of 318°-319° C. are obtained.

We claim:

1. A process for the preparation of 1,4-bis(4-hydroxybenzoyl)benzene of the formula (I)

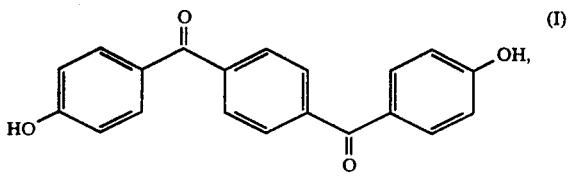

which comprises reacting a 1,4-bis(4-halobenzoyl)-benzene of the formula (II)

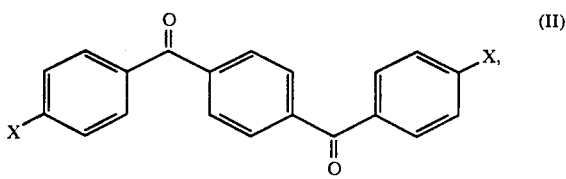

in which X is a fluorine, chlorine or bromine atom, with an alkali metal hydroxide or alkaline earth metal hydroxide or with a mixture of these hydroxides in an amount of about 200 to about 500 mol percent per halogenatom to be replaced, in a solvent which is inert to the reaction conditions and not miscible with water or in a two phase system of water and said inert organic solvent at temperatures of about 100° C. to about 250° C., if appropriate in the presence of a phase transfer catalyst.

2. The process as claimed in claim 1, wherein the reaction is carried out at temperatures of about 150° to about 220° C.

3. The process as claimed in claim 1, wherein the reaction is carried out with lithium hydroxide, sodium hydroxide, potassium hydroxide, calcium hydroxide or magnesium hydroxide or mixtures thereof.

4. The process as claimed in claim 1, wherein the reaction is carried out with about 200 to about 250 mol percent of alkali metal hydroxide or alkaline earth metal hydroxide per halogen atom to be replaced.

5. The process as claimed in claim 1, wherein the reaction is carried out in chlorobenzene, dichlorobenzene, trichlorobenzene, xylene or thereof toluene or N-methylpyrrolidone as the inert solvent.

6. The process as claimed in claim 1 wherein the reaction is carried out in a two-phase system composed of water and an inert organic solvent.

7. The process as claimed in claim 1, wherein the reaction is carried out in an aqueous two-phase system composed of water and chlorobenzene, dichlorobenzene, trichlorobenzene, xylene, toluene or chlorotoluene.

8. The process as claimed in claim 1, wherein the reaction is carried out in the presence of a quaternary ammonium or phosphonium compound, a pyridinium compound or a crown ether as the phase transfer catalyst.

9. The process as claimed in claim 1, wherein the reaction is carried out in the presence of a phase transfer catalyst selected from the group consisting of tetraalkylammonium chloride, tetraalkylammonium bromide, tetraalylphosphonium chloride, tetraalkylphosphonium bromide, tetraphenylphosphonium chloride, tetraphenylphosphenyl bromide, distearyldimethylammonium chloride, distearyldimethylammonium bromide, hexadecyltributylphosphonium chloride, hexadecyltributylphosphonium bromide, pyridinium chloride, and pyridinium bromide.

10. The process as claimed in claim 1, wherein the reaction time is between about 2 to about 12 hours.

11. The process as claimed in claim 10, wherein the phase transfer catalyst is in an amount from about 0.5 to about 30% by weight, relative to the hydroxide.

12. The process as claimed in claim 11, wherein the solvent is selected from the group consisting of chlorobenzene, dichlorobenzene, trichlorobenzene, xylene, toluene and chlorotoluene.

* * * * *